US00PP31267P2

(12) United States Plant Patent
Heimovaara

(10) Patent No.: US PP31,267 P2
(45) Date of Patent: Dec. 24, 2019

(54) ***CELOSIA* PLANT NAMED 'ZANCEMEPUR'**

(50) Latin Name: *Celosia argentea*
Varietal Denomination: Zancemepur

(71) Applicant: Sjoukje Heimovaara, Oegstgeest (NL)

(72) Inventor: Sjoukje Heimovaara, Oegstgeest (NL)

(73) Assignee: Van Zanten Breeding B.V., Rijsenhout (NL)

( * ) Notice: Subject to any disclaimer, the term of this patent is extended or adjusted under 35 U.S.C. 154(b) by 0 days.

(21) Appl. No.: 16/350,641

(22) Filed: Dec. 14, 2018

(51) Int. Cl.
*A01H 5/02* (2018.01)
*A01H 6/02* (2018.01)

(52) U.S. Cl.
USPC ..... Plt./263.1
CPC ..... *A01H 6/02* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Celosia* plant named 'Zancemepur', characterized by its compact and upright plant habit; freely branching habit; dark green and purple-colored leaves; freely flowering habit; bright purple-colored flowers arranged on spicate-type inflorescences; and good garden performance.

2 Drawing Sheets

Botanical designation: *Celosia argentea.*
Cultivar denomination: 'Zancemepur'.

BACKGROUND OF THE INVENTION

The present invention relates to a new and distinct cultivar of *Celosia* plant, botanically known as *Celosia argentea* and hereinafter referred to by the name 'Zancemepur'.

The new *Celosia* plant is a product of a planned breeding program conducted by the Inventor in Rijsenhout, The Netherlands. The objective of the breeding program is to create new compact and uniform *Celosia* plants with attractive and unique leaf and flower coloration.

The new *Celosia* plant originated from a cross-pollination made by the Inventor in Rijsenhout, The Netherlands in September, 2013 of a proprietary *Celosia argentea* selection identified as code number 13-0044-06, not patented, as the female, or seed, parent with a proprietary *Celosia argentea* selection identified as code number 2014-12, not patented, as the male, or pollen, parent. The new *Celosia* plant was discovered and selected by the Inventor as a single flowering plant from within the progeny of the stated cross-pollination in a controlled greenhouse environment in Rijsenhout, The Netherlands in June, 2014.

Asexual reproduction of the new *Celosia* plant by cuttings in a controlled greenhouse environment in Rijsenhout, The Netherlands since September, 2014 has shown that the unique features of this new *Celosia* plant are stable and reproduced true to type in successive generations.

SUMMARY OF THE INVENTION

Plants of the new *Celosia* have not been observed under all possible environmental conditions and cultural practices. The phenotype may vary somewhat with variations in environmental such as temperature and light intensity without, however, any variance in genotype.

The following traits have been repeatedly observed and are determined to be the unique characteristics of 'Zancemepur'. These characteristics in combination distinguish 'Zancemepur' as a new and *Celosia* plant:

1. Compact and upright plant habit.
2. Freely branching habit.
3. Dark green and purple-colored leaves.
4. Freely flowering habit.
5. Bright purple-colored flowers arranged on spicate-type inflorescences.
6. Good garden performance.

Plants of the new *Celosia* differ primarily from plants of the female parent selection in the following characteristics:

1. Plants of the new *Celosia* are more compact than plants of the female parent selection.
2. Plants of the new *Celosia* are more freely flowering than plants of the female parent selection.

Plants of the new *Celosia* differ primarily from plants of the male parent selection in plant habit as plants of the new *Celosia* are more uniform than plants of the male parent selection.

Plants of the new *Celosia* can be compared to plants of *Celosia hybrida* 'Zancecomfort', disclosed in U.S. Plant Pat. No. 25,154. In side-by-side comparisons, plants of the new *Celosia* and 'Zancecomfort' differ primarily in the following characteristics:

1. Plants of the new *Celosia* are not as freely flowering as plants of 'Zancecomfort'.
2. Plants of the new *Celosia* and 'Zancecomfort' differ in flower color as plants of the new *Celosia* have purple-colored flowers whereas plants of 'Zancecomfort' have bright red purple-colored flowers.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type.

Colors in the photographs may differ slightly from the color values cited in the detailed botanical description which accurately describe the colors of the new *Celosia* plant.

The photograph on the first sheet comprises a side perspective view of a typical flowering plant of 'Zancemepur' grown in a container.

The photograph on the second sheet is a close-up view of a typical plant of 'Zancemepur' showing the leaf coloration.

DETAILED BOTANICAL DESCRIPTION

The aforementioned photographs and following observations, measurements and values describe plants grown during the spring and summer in 9-cm containers in a glass-covered greenhouse in Rijsenhout, The Netherlands and under cultural practices typical of commercial production. During the production of the plants, day and night temperatures ranged from 20° C. to 22° C. and light levels averaged 2,500 lux. Plants were pinched one time about 2.5 weeks after planting and were ten weeks old when the photographs and description were taken. In the following description, color references are made to The Royal Horticultural Society Colour Chart, 2015 Edition, except where general terms of ordinary dictionary significance are used.

Botanical classification: *Celosia argentea* 'Zancemepur'.

Parentage:

*Female, or seed, parent.*—Proprietary *Celosia argentea* selection identified as code number 13-0044-06, not patented.

*Male, or pollen, parent.*—Proprietary *Celosia argentea* selection identified as code number 2014-12, not patented.

Propagation:

*Type.*—By terminal cuttings.

*Time to initiate roots, summer.*—About 12 days at temperatures about 21° C.

*Time to produce a rooted young plant, summer.*—About 19 days at temperatures about 21° C.

*Root description.*—Fine, fibrous and fleshy; close to 199D in color.

*Rooting habit.*—Freely branching; dense.

Plant description:

*Plant form and growth habit.*—Herbaceous annual typically grown as a potted plant; compact and broadly upright plant habit; freely branching habit with about six lateral branches developing per plant; moderately vigorous.

*Plant height.*—About 21 cm to 23 cm.

*Plant width(spread).* —About 23 cm to 25 cm.

*Lateral branches.*—Length: About 18 cm to 21 cm. Diameter: About 5 mm to 6 mm. Internode length: About 0.8 cm to 2 cm. Texture: Smooth, glabrous. Color: Close to 145B; streaks, close to 185D.

Leaf description:

*Arrangement.*—Alternate; simple.

*Length.*—About 5 cm to 13 cm.

*Width.*—About 2.8 cm to 6 cm.

*Shape.*—Elliptic to broadly elliptic.

*Apex.*—Acuminate.

*Base.*—Attenuate to truncate.

*Margin.*—Entire.

*Texture, upper and lower surfaces.*—Smooth, glabrous.

*Venation pattern.*—Pinnate.

*Color.*—Developing leaves, upper surface: Close to 138A. Developing leaves, lower surface: Close to 138B. Fully expanded leaves, upper surface: Close to 137A; random sectors and spots, close to N79A; venation, close to 149D. Fully expanded leaves, lower surface: Close to 138B; random sectors and spots, close to N77D; venation, close to 195A.

*Petioles.*—Length: About 1 cm to 3 cm. Diameter: About 1 cm to 3 cm. Texture, upper and lower surfaces: Smooth, glabrous. Color, upper surface: Close to 149D. Color, lower surface: Close to 195A.

Flower description:

*Flower type and flowering habit.*—Single elliptical flowers arranged in terminal and axillary spikes; spicate-type inflorescences; flowers face mostly upright; freely flowering habit, about 80 to 120 flowers per inflorescence and about 5,000 flowers developing per plant.

*Fragrance.*—None detected.

*Natural flowering season.*—Plants begin flowering about 5.5 weeks after planting; in the garden, plants flower continuously during the summer in The Netherlands.

*Postproduction longevity.*—Inflorescences last about two months on the plant; flowers persistent.

*Inflorescence height.*—About 2.5 cm to 6 cm.

*Inflorescence diameter.*—About 1 cm to 1.8 cm.

*Flower diameter.*—About 2 mm.

*Flower depth.*—About 6 mm.

*Flower buds.*—Length: About 3 mm. Diameter: About 1 mm. Shape: Elliptical. Color: Close to 71B.

*Petals.*—None observed.

*Sepals.*—Quantity per flower: Typically five. Length: About 5 mm. Width: About 1 mm. Shape: Lanceolate. Apex: Acute. Base: Attenuate. Margin: Entire. Texture, upper and lower surfaces: Smooth, glabrous. Color: When opening and fully opened, upper surface: Close to N78A; color does not fade with development. When opening and fully opened, lower surface: Close to N78A; color does not fade with development.

*Pedicels.*—Length: About 5 mm. Diameter: About 2 mm. Angle: About 45° from vertical. Strength: Weak; flexible. Texture: Smooth, glabrous. Color: Close to 145B.

*Reproductive organs.*—Stamens: Quantity per flower: Typically five. Filament length: About 2 mm. Filament color: Close to N74B. Anther length: About 2 mm. Anther color: Close to 158D. Pollen, amount: Moderate. Pollen color: Close to 156D. Pistils: Quantity per flower: One. Pistil length: About 4 mm. Style length: About 3 mm. Style color: Close to N78A. Stigma color: Close to N78A. Ovary color: Close to N78D. Seeds: Length: About 1.5 mm. Diameter: About 1.5 mm. Color: Close to 202A.

Pathogen & pest resistance: To date, plants of the new *Celosia* have not been noted to be resistant to pathogens and pests common to *Celosia* plants.

Garden performance: Plants of the new *Celosia* have been observed to have good garden performance and tolerate rain, wind and temperatures ranging from about 10° C. to 30° C.

It is claimed:

1. A new and distinct *Celosia* plant named 'Zancemepur' as illustrated and described.

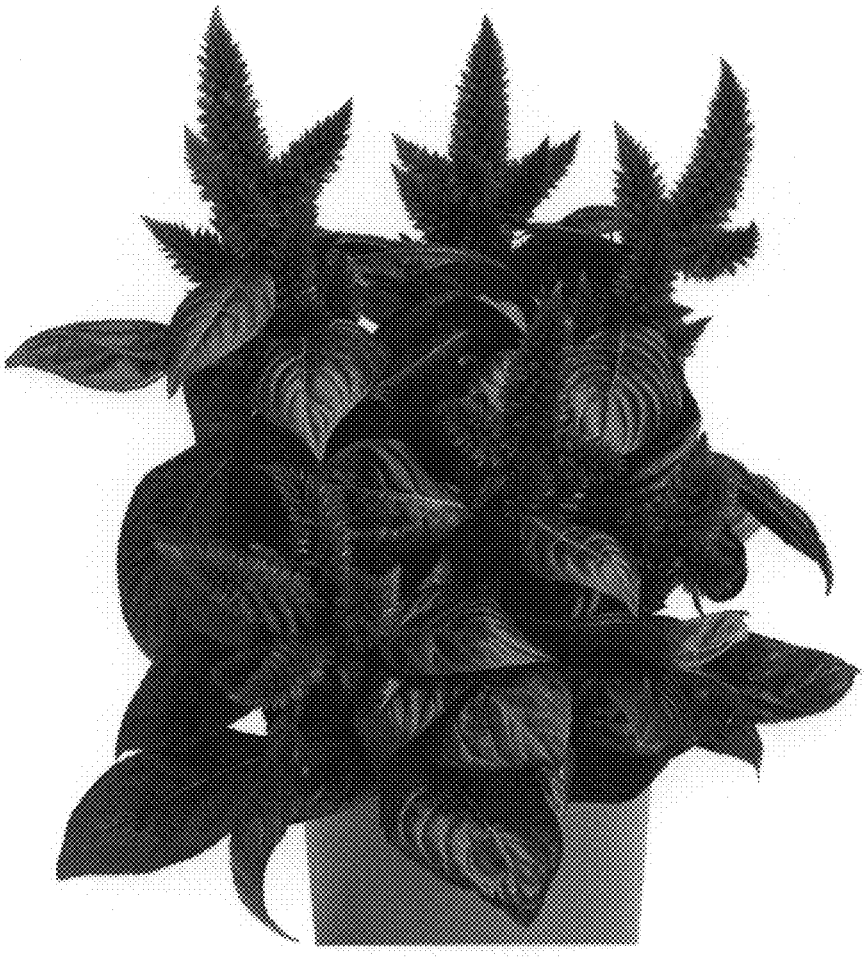

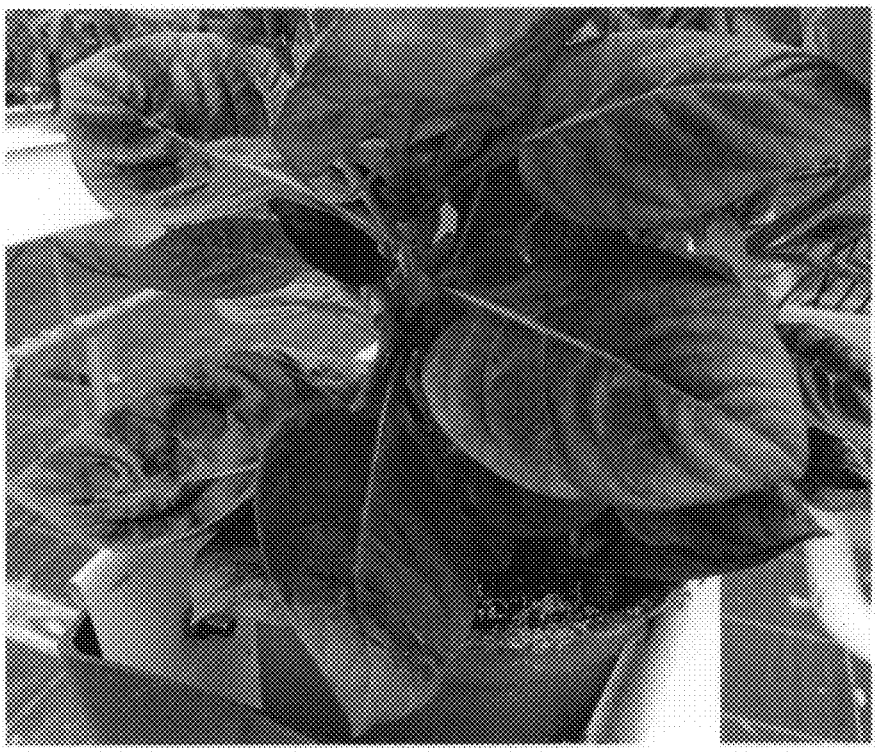

* * * * *